US010905732B2

(12) United States Patent
McCausland et al.

(10) Patent No.: US 10,905,732 B2
(45) Date of Patent: *Feb. 2, 2021

(54) TRANSFER FACTOR PREPARATIONS AND ASSOCIATED METHODS

(71) Applicant: 4LIFE PATENTS, LLC, Sandy, UT (US)

(72) Inventors: Calvin W. McCausland, Springville, UT (US); Brent Vaughan, Kearns, UT (US); David Lisonbee, Boise, ID (US); William J. Hennen, Eagle Mountain, UT (US)

(73) Assignee: 4Life Patents, LLC, Sandy, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/968,663

(22) Filed: May 1, 2018

(65) Prior Publication Data

US 2018/0318369 A1 Nov. 8, 2018

Related U.S. Application Data

(63) Continuation of application No. 11/415,837, filed on May 2, 2006, now Pat. No. 9,956,258.

(60) Provisional application No. 60/677,226, filed on May 2, 2005.

(51) Int. Cl.
| *A61K 36/889* | (2006.01) |
| *A61K 36/87* | (2006.01) |
| *A61K 36/35* | (2006.01) |
| *A23L 33/105* | (2016.01) |
| *A23L 33/17* | (2016.01) |
| *A23L 33/19* | (2016.01) |
| *A23G 4/12* | (2006.01) |
| *A23L 2/02* | (2006.01) |
| *A23L 2/38* | (2021.01) |
| *A23L 2/52* | (2006.01) |
| *A23L 2/66* | (2006.01) |
| *A61K 36/185* | (2006.01) |
| *A61K 38/19* | (2006.01) |

(52) U.S. Cl.
CPC ............ *A61K 36/35* (2013.01); *A23G 4/12* (2013.01); *A23L 2/02* (2013.01); *A23L 2/38* (2013.01); *A23L 2/52* (2013.01); *A23L 2/66* (2013.01); *A23L 33/105* (2016.08); *A23L 33/17* (2016.08); *A23L 33/19* (2016.08); *A61K 36/185* (2013.01); *A61K 36/87* (2013.01); *A61K 38/19* (2013.01); *A23V 2002/00* (2013.01)

(58) Field of Classification Search
CPC .................... A61K 36/889; A61K 36/87
USPC ........................ 424/727, 766, 777
See application file for complete search history.

(56) References Cited

U.S. PATENT DOCUMENTS

| 3,692,532 | A | * | 9/1972 | Shenkenberg | ....... A23C 9/1542 |
| | | | | | 426/584 |
| 3,851,051 | A | | 11/1974 | Miskel et al. | |
| 4,810,827 | A | | 3/1989 | Mitsuhashi et al. | |
| 4,816,563 | A | | 3/1989 | Wilson et al. | |
| 5,252,333 | A | * | 10/1993 | Horrobin | ............... A01N 37/06 |
| | | | | | 424/422 |
| 5,585,098 | A | | 12/1996 | Coleman | |
| 5,648,092 | A | | 7/1997 | Weckenmann et al. | |
| 5,773,232 | A | | 6/1998 | Wier | |
| 5,846,532 | A | * | 12/1998 | Kline | ..................... A61K 38/45 |
| | | | | | 424/94.6 |
| 5,928,686 | A | | 7/1999 | Ivey et al. | |
| 6,030,622 | A | * | 2/2000 | Shehadeh | ............ A61K 36/185 |
| | | | | | 424/439 |
| 6,147,624 | A | | 11/2000 | Clapper | |
| 6,210,681 | B1 | | 4/2001 | Walker et al. | |
| 6,258,383 | B1 | | 7/2001 | Gohlke et al. | |
| 6,326,028 | B1 | | 12/2001 | Nivaggioli et al. | |
| 6,468,534 | B1 | | 10/2002 | Hennen et al. | |
| 6,630,316 | B1 | | 10/2003 | Wier | |
| 6,733,781 | B2 | | 5/2004 | Abu-Izza et al. | |
| 6,811,793 | B2 | | 11/2004 | Wehling | |
| 6,866,868 | B1 | * | 3/2005 | Lisonbee | ................ A61J 3/074 |
| | | | | | 424/535 |
| 7,094,415 | B2 | | 8/2006 | Marenick | |
| 7,169,571 | B2 | | 1/2007 | Wier | |
| 2002/0034563 | A1 | | 3/2002 | Grassin et al. | |

(Continued)

FOREIGN PATENT DOCUMENTS

| CN | 1583164 A | 2/2005 |
| DE | 121707 A | 8/1976 |

(Continued)

OTHER PUBLICATIONS

Slater: Who's Drinking What: Sunday Times. London. May 16, 2004, p. 44.*

(Continued)

*Primary Examiner* — Michael Barker
*Assistant Examiner* — Deborah A Davis
(74) *Attorney, Agent, or Firm* — Durham Jones & Pinegar, P.C., Intellectual Property Law Group

(57) ABSTRACT

A drink includes an edible liquid or semisolid preparation and transfer factor. The drink may also include lactoferrin and one or more preservatives. An edible preparation includes a fruit component and transfer factor. The fruit component may include at least one oligoproanthocyanidin-containing fruit. The edible preparation may also include lactoferrin. One or more preservatives may also be included in the edible preparation. The drink or the edible preparation may be sterilized or pasteurized.

20 Claims, No Drawings

(56) References Cited

U.S. PATENT DOCUMENTS

| | | |
|---|---|---|
| 2002/0044942 A1 | 4/2002 | Dopson |
| 2003/0077254 A1 | 4/2003 | Ramaekers |
| 2007/0098869 A1 | 5/2007 | Foster et al. |
| 2008/0081076 A1 | 4/2008 | Lisonbee et al. |
| 2009/0162517 A1 | 6/2009 | Lai et al. |

FOREIGN PATENT DOCUMENTS

| | | |
|---|---|---|
| EP | 1 106 068 A2 | 6/2001 |
| EP | 1 602 653 A1 | 12/2005 |
| JP | 2005-068060 | 3/2005 |
| JP | 2005527234 | 9/2005 |
| JP | 2006-520804 | 9/2006 |
| JP | 2007-505913 | 3/2007 |
| WO | 1997020548 A1 | 6/1997 |
| WO | 2000059519 A2 | 10/2000 |
| WO | 2002017732 A2 | 3/2002 |
| WO | 2003101225 A2 | 12/2003 |
| WO | 2004017916 A2 | 3/2004 |
| WO | 2004041071 A2 | 5/2004 |
| WO | 2004080995 A1 | 9/2004 |
| WO | 2004084833 A2 | 10/2004 |
| WO | 2004112491 A2 | 12/2004 |
| WO | 2005028622 A2 | 3/2005 |
| WO | 2006119408 A1 | 11/2006 |

OTHER PUBLICATIONS

International Search Report, PCT/US2006/017118, dated Sep. 13, 2006.
"Announcing 4Life Transfer Factor RioVida with Acai Berry," http://web.archive.org/web/20050413042215/http://www.acaiberries.com/index.html, accessed Oct. 25, 2007.
"Food Protection Program," http://archive.org/web/20040221222150/http://www.metrokc.gov/health/foodsfty/pasturizedjuice.htm, Feb. 21, 2004, accessed Oct. 25, 2007.
International Search Report, PCT/US2007/078947, dated Aug. 22, 2008.
Bates, R.P., et al., "Principles and Practices of Small and Medium Scale Fruit Juice Processing," Food and Agricultural Organization of the United Nations (FAO) Services Bulletin 146 (Rome, 2001).
Hoover, D.G., "Minimally Processed Fruits and Vegetables: Reducing Microbial Load by Nonthermal Physical Treatments," Food Tech. 57(6): 66-69, 71 (1997).
Peters, R.L., et al., "Assay in the Mouse for Delayed-Type Hypersensitivity to Murine Leukemia Virus," J. Natl. Cancer Inst. 55(5): 1089-95 (Nov. 1975).
Beecher, G.R., "Proanthocyanidins: Biological Activities Associated with Human Health," Pharmaceutical Biol. 42 (Supplement): 2-20 (2004).
"RioVida—Liquid Transfer Factor in Acai Berry Juice," http://web.archive.org/web/20050416024521/http://www.globalsuccess4life.com/riovida.html, Apr. 16, 2005, accessed Jun. 8, 2013.
European Patent Office, Supplementary European Search Report dated Jul. 24, 2009 in corresponding European application No. 06759033.1, which is a national stage application corresponding to International Application PCT/US2006/017118.
Brown, T.A., "Immunity at Mucosal Surfaces," Advances in Dental Research 10:62 (1996).
Strunz, U., "Forever Young: Fitness Drinks: Get Fit, Stay Young and Keep Slender with Protein-packed Power Drinks," Silverback Books, pp. 23 and 34 (2001).
Wolfe, F.A., "The Complete Idiot's Guide to Herbal Remedies," p. 146 (Penguin, 1999).
Mazo, "The Immune Advantage: The Powerful, Natural Immune-boosting Program to Help you Prevent Disease, Enhance Vitality, Live Longer, Healthier Life," p. 307 (Rodale,2001).
Bricklin, M. "Prevention Magazine's Nutrition Advisor: The Ultimate Guide to Health-Boosting and Health-Harming Factors in Your Diet," p. 301 (Rodale, 1994).
Challem, J. "User's Guide to Nutritional Supplements," p. 261 (Basic Health Publications, Inc., 2003).
http://pharmlabs.unc.edu/tablets/text.htm.
dictionary.reference.com, http://dictionary.reference.com/browse/food, Accessed Oct. 25, 2011.
Danish Patent and Trademark Office, "Singapore Search Report and Written Opinion," dated May 17, 2013, in related Singapore application No. 201100707-7.
Hagerman, A.E., et al., "the Specificity of Proanthocyanidin Protein Interactions," J. Biol. Chem., 256(9): 4494-97 (1981).
"Colostrum," http://en.www.wikipedia.org/wiki/Colostrum.
IP Australia, Examiner's Report dated Mar. 25, 2011 in related Australian application No. 2006242106.
State Intellectual Property Office of China, English translation of First Office Action dated Aug. 10, 2010 in related Chinese application No. 200680021004.1.
State Intellectual Property Office of China, English translation of Second Office Action dated Jan. 11, 2012 in related Chinese application No. 200680021004.1.
State Intellectual Property Office of China, English translation of Notification of Reexamination dated Jul. 3, 2013 in related Chinese application No. 200680021004.1.
State Intellectual Property Office of China, English translation of First Office Action dated Aug. 1, 2016 in related Chinese application No. 201410247204.5.
State Intellectual Property Office of China, English translation of Second Office Action dated Jun. 16, 2017 in related Chinese application No. 201410247204.5.
State Intellectual Property Office of China, English translation of Third Office Action dated Jan. 5, 2018 in related Chinese application No. 201410247204.5.
European Patent Office, Communication pursuant to Article 94(3) EPC dated Jun. 11, 2009 in related European application No. 06759033.1.
European Patent Office, Communication pursuant to Article 94(3) EPC dated Jan. 27, 2011 in related European application No. 06759033.1.
European Patent Office, Communication pursuant to Article 94(3) EPC dated Mar. 28, 2012 in related European application No. 06759033.1.
European Patent Office, Communication pursuant to Article 94(3) EPC dated Mar. 10, 2014 in related European application No. 06759033.1.
European Patent Office, Communication pursuant to Article 94(3) EPC dated Feb. 3, 2015 in related European application No. 06759033.1.
European Patent Office, Communication pursuant to Article 94(3) EPC dated Oct. 19, 2016 in related European application No. 06759033.1.
Japanese Patent Office, English Translation dated Sep. 3, 2010 of First Office Action in related Japanese application No. 2008-510197.
Japanese Patent Office, English Translation dated Apr. 8, 2011 of Second Office Action in related Japanese application No. 2008-510197.
Japanese Patent Office, English Translation dated Dec. 27, 2011 of Third Office Action in related Japanese application No. 2008-510197.
Mexican Patent Office, English Summary dated Jan. 20, 2011 of First Office Action in related Mexican application No. MX/a/2007/013850.
Mexican Patent Office, English Summary dated Jun. 21, 2011 of Second Office Action in related Mexican application No. MX/a/2007/013850.
Intellectual Property Office of the Philippines, Bureau of Patents, Substantive Examination Report dated Apr. 2, 2012 in related Filipino application No. 1/2007/502430.
Intellectual Property Office of the Philippines, Bureau of Patents, Subsequent Substantive Examination Report dated May 17, 2013 in related Filipino application No. 1/2007/502430.
Intellectual Property Office of the Philippines, Bureau of Patents, Subsequent Substantive Examination Report dated Aug. 23, 2013 in related Filipino application No. 1/2007/502430.

(56) References Cited

OTHER PUBLICATIONS

Xiang, C, et al, "P-transfer factor for oral solution," Pediatric Drug Handbook 241 (Beijing Science Press 2002-2007).
Chuanhe, T., Bioactive Substance from Plants 275 & 288 (Chemical Industry Press, Jan. 31, 2005).
Chinese National Intellectual Property Adminstration, "Rejection Decision," Chinese patent application No. 201410247204.5, dated Mar. 18, 2020.

* cited by examiner

TRANSFER FACTOR PREPARATIONS AND ASSOCIATED METHODS

CROSS-REFERENCE TO RELATED APPLICATIONS

This application is a continuation of U.S. patent application Ser. No. 11/415,837, filed on May 2, 2006, titled TRANSFER FACTOR PREPARATIONS AND ASSOCIATED METHODS, now U.S. Pat. No. 9,956,258, issued May 1, 2018, which claims the benefit of U.S. Provisional Patent Application No. 60/677,226 filed on May 2, 2005, titled TRANSFER FACTOR PREPARATIONS AND ASSOCIATED METHODS. The entire disclosure of each of the foregoing patent applications is hereby incorporated herein.

FIELD OF THE INVENTION

The present invention relates generally to preparations that include transfer factor and, more specifically, to edible preparations, such as drinks and solids that include transfer factor. Additionally, the present invention relates to methods for manufacturing edible, transfer factor-containing preparations and to methods that include administration of such preparations.

SUMMARY OF THE INVENTION

In one aspect, the present invention includes a drink that includes transfer factor. The drink includes an edible liquid or semisolid component and transfer factor. The liquid or semisolid component may comprise a fruit juice, a gelatin, a dairy-based product, or any other suitable, drinkable composition with components that are compatible with transfer factor. When mixed with the liquid component, the transfer factor may retain substantially all of one or more of its activities (e.g., components of the liquid component may not interfere with one or more activities of transfer factor), or one or more of the activities of transfer factor may actually be enhanced by one or more components of the liquid component of the drink.

In another aspect, the present invention includes a composition with a fruit component and transfer factor. The fruit component may include at least one oligoproanthocyanidin ("OPC")-containing fruit or an extract thereof. The term "extract" is broadly defined herein, including any OPC-including part of a fruit. Examples of extracts include, without limitation, juices (dilute, normal concentration, or concentrate), dehydrated fruit, and powders including one or more components of the fruit. Such a composition may be in a liquid form or a solid form, including but not limited to solid forms that are configured for at least partial dissolution or digestion in the mouth of a subject.

Another aspect of the present invention includes a process for making an edible preparation that includes transfer factor. The process includes mixing a fruit component with transfer factor. Preservatives may also be included in the mixture. The mixture may be chilled to prevent microbial growth. To further prevent microbial growth, the mixture may be pasteurized before chilling. Alternatively, the mixture may be sterilized.

Other features and advantages of the present invention will become apparent to those of ordinary skill in the art through consideration of the ensuing description and the appended claims.

DETAILED DESCRIPTION

An exemplary embodiment of a drink that includes transfer factor may be liquid or semisolid. Such a drink may include an edible liquid or semisolid component, as well as transfer factor. The liquid or semisolid component may, by way of nonlimiting example, comprise a fruit juice, a gelatin, a dairy-based product, or any other suitable, drinkable composition with components that are compatible with transfer factor. When mixed with the liquid component, the transfer factor may retain substantially all of one or more of its activities (e.g., components of the liquid component may not interfere with one or more activities of transfer factor), or one or more of the activities of transfer factor may actually be enhanced by one or more components of the liquid component of the drink. Such a drink may also include one or more preservatives. Alternatively, or in addition, lactoferrin may be included in a drink that includes transfer factor.

Another embodiment of an edible preparation that includes transfer factor also includes a fruit component. The edible preparation may also include one or more preservatives. Alternatively, or in addition, lactoferrin may be included in such an edible composition.

The fruit component includes at least one fruit that naturally includes OPC or a juice or other extract of such a fruit. By way of nonlimiting example, the fruit component may include one or more of acai, elderberry, grape, and pomegranate or an extract thereof. OPC is a known antioxidant and may, therefore, be useful in neutralizing or otherwise acting against free radicals and other oxidants, which may adversely affect cell membranes, cause accelerated cellular aging, and are known or believed to be at least indirectly responsible for a wide variety of disease states, as well as compromised immunity, in living beings.

The transfer factor component may include any type of transfer factor, as well as a combination of two or more types of transfer factor. For example, avian transfer factor, bovine transfer factor, or any other type of transfer factor may be included in the transfer factor component. The transfer factor of the transfer component factor may be derived from any suitable, acceptable source. For example, avian transfer factor may be obtained from eggs, such as by a process disclosed in U.S. Pat. No. 6,468,534 to Hennen et al. (hereinafter "Hennen"), the disclosure of which is hereby incorporated herein, in its entirety, by this reference. An example of the manner in which bovine transfer factor may be obtained is disclosed in U.S. Pat. No. 4,816,563 to Wilson et al. (hereinafter "Wilson"), the disclosure of which is hereby incorporated herein, in its entirety, by this reference. Compositions that include two or more types of transfer factor, as well as processes for combining and processing two or more types of transfer factor, are disclosed in U.S. Pat. No. 6,866,868 to Lisonbee et al. (hereinafter "Lisonbee"), the disclosure of which is hereby incorporated herein, it its entirety, by this reference.

Transfer factor is known or believed to improve the oxidative balance of a living being, as well as to enhance the effectiveness of antioxidants, as demonstrated by the disclosure of the international patent application filed pursuant to the Patent Cooperation Treaty and having International Publication Number WO 2004/041071 A2 (hereinafter "Dadali"), the disclosure of which is hereby incorporated herein, in its entirety, by this reference.

An edible preparation according to the present invention may also include one or more preservatives. Suitable preservatives, such as those accepted for use in foods and beverages, may be used. Examples of preservatives that may be included in an edible preparation of the present invention include, but are not limited to, sodium benzoate and preservatives from the paraben family of chemicals.

Lysozyme, when used in an edible preparation that incorporates teachings of the present invention, acts as a preservative. While lysozyme has been used as a preservative in cheeses, it is not believed to have been previously used in this capacity in edible preparations that include fruits or extracts thereof.

Lactoperoxidase may also, or alternatively, be included in edible preparations that incorporate teachings of the present invention. Lactoperoxidase is another preservative that has been used in dairy products, but it is believed that lactoperoxidase has not been used to preserve edible compositions that include fruits or extracts of fruits.

Lactoferrin is known or believed to stimulate the immune system and may work in concert with transfer factor to improve the immunity of a subject that receives an edible preparation that incorporates teachings of the present invention. Lactoferrin is also known to starve bacteria and, thus, may act as a preservative when included in an edible preparation that incorporates teachings of the present invention.

In an exemplary embodiment, the edible preparation may be a liquid, a semisolid, or a solid. A liquid form of edible preparation may be in the form of a fruit juice. A solid form of edible preparation may be configured for consumption as a solid (e.g., as a chewable tablet, an effervescent tablet, a dissolvable wafer, a dissolvable gel strip, etc.), for reconstitution as a liquid, or in any other suitable fashion.

A liquid edible preparation that incorporates teachings of the present invention is described in the following example:

Example 1

An example of a formulation for a liquid edible preparation that includes transfer factor follows:

TABLE 1

| Ingredient | % of Total (w/v) | Density (g/ml) | % of Total Juices (v/v) |
|---|---|---|---|
| Water | 76.681 | 1.000 | |
| Apple Juice | 5.146 | 1.346 | 19 |
| Purple Grape Juice | 5.100 | 1.330 | 19 |
| Glycerin | 3.980 | 1.249 | |
| Blueberry Juice | 3.772 | 1.315 | 18 |
| Transfer Factor E-XF | 1.912 | | |
| Pomegranate Juice | 1.480 | 1.315 | 15 |
| Grape color concentrate (e.g., MEGANATURAL ™ purple from Canandaigua Concentrates & Colors, a Division of Canandaigua Wine Company of Madera, California) | 0.500 | 1.306 | |
| Vitamin C | 0.498 | | |
| Elderberry Juice | 0.419 | 1.315 | 15 |
| Flavorings | | | |
| Berry flavor (BE-01407) | 0.198 | 1.000 | |
| Berry flavor (BE-01271) | 0.055 | 1.000 | |
| Natural *Vanilla* (VA-01239) | 0.165 | 1.000 | |
| Acai Powder | 0.318 | | 14 |
| Lactoferrin | 0.191 | | |
| Lysozyme | 0.014 | | |
| Lactoperoxidase | 0.003 | | |

Transfer Factor E-XF includes bovine transfer factor from cow colostrum and avian transfer factor from the yolk of a chicken's egg.

The flavorings listed in TABLE 1 are available from Flavors Inc.

A daily dosage of about one fluid ounce (about 30 ml) or more of a composition with ingredients in the proportions listed in TABLE 1 may be administered to or consumed by a subject. In addition to the numerous known and believed benefits of antioxidants, including the benefits of OPC and OPC-containing fruits such as acai, administration or consumption of an edible composition that incorporates teachings of the present invention provides the subject with the additional and sometimes synergistic beneficial affects of transfer factor, which are known in the art, as evidenced by the disclosures of Dadali, Hennen, Lisonbee, and Wilson.

An edible preparation may be made by mixing components of a food base with transfer factor by processes that are known in the art. Additionally, lactoferrin or preservatives, including without limitation lysozyme, lactoperoxidase, and other food preservatives, may be mixed with the food base.

Of course, the types of processes that are used and, possibly, the order in which certain ingredients are included, may depend in part upon the form, or state (e.g., liquid, solid, semisolid, etc.), of the various ingredients that are mixed with one another, their solubilities, and the desired form, or state, of the resulting edible preparation (i.e., whether the edible preparation is liquid, semisolid, solid, includes carbonation, etc.). Suitable processes that may be used to manufacturing edible preparations of a variety of different forms are well known and within the skill of those in the relevant art.

A liquid edible preparation may be manufactured with liquid ingredients or liquid and dissolvable solid (e.g., powder, crystalline, etc.) or semisolid (e.g., gel, paste, etc.) ingredients. Alternatively, dry ingredients may be mixed with one another, then reconstituted (e.g., in water, juice, etc.) by either the manufacturer, a distributor, or an end-user to liquid form.

Known techniques, such as those disclosed in "Principles and Practices of Small- and Medium-Scale Fruit Juice Processing," Food and Agricultural Organization of the United Nations (FAO) Services Bulletin 146 (Rome, 2001), the entire disclosure of which is hereby incorporated herein by this reference, may be used in one or more parts of a process for manufacturing fluid edible preparations that incorporate teachings of the present invention.

A solid or semisolid edible preparation may be manufactured with dry, semisolid, or liquid components, or combinations thereof, then, if desired, dried (e.g., by dehydration processes, etc.) to a desired state. A solid edible preparation may be manufactured in any suitable form (e.g., chewable tablet, dissolvable wafer or gel, chewing gum, reconstitutable powder, etc.) by processes that are well known in the art. Of course, various additional ingredients (e.g., fillers, sweeteners, wicking agents, etc.) may be used to facilitate manufacture of the edible preparation in a desired solid form. Examples of additional ingredients that may be included in a solid or semisolid edible preparation include, but are not limited to, one or more of the following: pullulan, corn starch, gelatin, dextrin, glycerin, carrageenan, xanthan gum, dextrose, corn syrup, and beeswax. The incorporation of additional ingredients into an edible composition is well within the skill of one who practices in the art.

Without limiting the scope of the present invention, various types of solid edible compositions may be formed by known processes, including, but not limited to, the processes that are disclosed at "Tablets," http://pharmlabs.unc.edu/tablets/text.htm and in U.S. Pat. No. 6,326,028 to Nivaggioli et al., U.S. Pat. No. 6,733,781 to Abu-Izza et al., and U.S.

Pat. No. 6,811,795 to Wehling, the disclosures of each of which are hereby incorporated herein, in their entireties, by this reference.

Processes that are used to manufacture edible preparations that are in a form that is not completely dry, such as a liquid or semisolid state, may be effected at a low temperature (e.g., between about 0° C. and about 10° C., at about 4° C., etc.), such as in a refrigerated environment, then transported and stored at such temperatures to reduce the likelihood of microbial growth or proliferation therein.

Alternatively, an edible preparation that is in a form that is not completely dry may be pasteurized or sterilized. Pasteurization processes, which decrease the number of microorganisms present, but do not entirely eliminate the microorganisms, improve the stability of products that are to be stored at reduced temperatures (e.g., frozen or refrigerated, or "chilled"). When an edible preparation is sterilized, all or substantially all microorganisms therein are killed or inactivated, facilitating prolonged storage of the edible preparation at room temperature or even higher temperatures.

As an example, an edible preparation that includes transfer factor may be sterilized by known superheated steam injection processes. The temperatures and durations of such processes depend, of course, upon the form and ingredients of the composition to be sterilized. When making a liquid preparation, the resulting edible preparation may be "flash" heated to a particular temperature (e.g., 250° F.) for a corresponding duration (e.g., two seconds). Alternatively, a sterilization or pasteurization process of different duration and temperature may be used, so long as the duration and temperature of the process are in substantial accord with a practice that has been accepted in the art, such as use of the following equation:

$$t_p = 5 \cdot 10^{14} \cdot e^{-0.4353 \cdot T_{mo}},$$

where $t_p$ is the minimum duration of the process, and $T_{mo}$ is the temperature at which the process is effected.

Of course, processes that reduce microbial load on an edible preparation of the present invention need not comprise heat-treatment techniques. Sterilization or other microbial load-reducing techniques that employ other means (e.g., filtration, antimicrobial ingredients, etc.) may also be used in manufacturing an edible preparation. Examples of suitable processes are disclosed in Hughes, D. E., and Nyborg, W., "Minimally Processed Fruits and Vegetables: Reducing Microbial Load by Nonthermal Physical Treatments," Food Technology 52(6): 66-71 (1997), the disclosure of which is hereby incorporated herein, in its entirety, by this reference.

It is desirable that, following pasteurization or sterilization, the transfer factor retain some if not substantially all or all of its activity. A variety of pasteurization or sterilization processes may be employed, including pasteurization or sterilization processes that may be used to reduce microbial counts or completely eliminate microorganisms from foods. As many sterilization processes are known to significantly reduce the activity of certain proteins, including antibodies, a study was performed to determine whether transfer factor retains at least some of its activity following sterilization.

In the study, mouse footpad assay techniques, similar to those disclosed in Natl. Cancer Inst. 55(5):1089-95 (November 1975), were used to determine the effects of heat pasteurization or sterilization processes (specifically, superheated steam injection processes) on edible preparations including transfer factor. Two sterilized samples were compared with an unsterilized sample, as well as with a negative control and a positive control.

Separate populations of six mice were tested for each of the five samples and controls. The tests were conducted in two phases, a first that immediately followed heat sterilization of the samples, and a second that was conducted after storing the two heat sterilized samples at a temperature of about 40° C. for about three months, which is well-accepted in the art to be the equivalent of about one year of storage at room temperature. Thirty different mice were used in each phase of the study. The following procedures were followed in each phase of the study In the positive control (i.e., the "fifth group"), fourteen days prior to testing, the footpads of the right rear feet of six BALB/c mice having ages of about nine weeks to about ten weeks were anesthetized with isoflurane. Then 0.02 ml of an about 50/50 (wt/wt) mixture of Freund's adjuvant and bovine rhinotracheitis virus diarrhea vaccine was administered intramuscularly to each mouse by way of two injections at the base of each side of the mouse's tail. This early injection of antigen allows the mice of the positive control group to elicit their own primary immune response and secondary, or delayed-type hypersensitivity response to the antigen. The mice of the other five groups were not preexposed to the antigen in this manner.

About twenty-four hours before evaluating the hind footpads of the mice, the six BALB/c mice of each group, which were of similar age to the mice of the positive control group, were anesthetized with isoflurane. About 0.5 ml of a sample solution or control solution was then administered by subcutaneous injection at the back of the neck of each mouse.

In the first group (see EXAMPLE 2 below), which was the negative control group, the back of the neck of each mouse was injected with about 0.5 ml of sterile saline solution.

In the second group (see EXAMPLE 3 below), the sample solution included 16% solids (w/v) of a reconstituted (in distilled, deionized water) lyophilized colostrum fraction that included transfer factor. The solution was set at a pH of 4.0, which was intended to estimate the pH of a fruit juice preparation (the actual pH of which is about 3.6 or about 3.7). Following reconstitution and pH adjustment, the solution was sterilized by heating the same to a temperature of 250° F. for about two seconds.

In the third group (see EXAMPLE 4 below), the sample solution included 16% solids (w/v) of a reconstituted (in distilled, deionized water) lyophilized colostrum fraction that included transfer factor. The pH of the resulting solution was not adjusted and, thus, was neutral (i.e., 7.0) or slightly basic (i.e., greater than 7.0)). Following reconstitution, the solution was sterilized by heating the same to a temperature of 250° F. for about two seconds.

In the fourth group (see EXAMPLE 5 below), the sample solution was a concentrate of a colostrum fraction that included transfer factor, which had been diluted to about 16% solids (w/v) in distilled, deionized water. This solution was not heat sterilized or pH adjusted.

The mice of the fifth group (see EXAMPLE 6 below), which was the positive control groups, respectively, received sterile saline solution.

At the start of the mouse footpad assay, the right hind footpad and the left hind footpad of each mouse were measured, such as with a Starrett gauge. The right hind footpad of each of the thirty mice during each phase of the study was then subcutaneously injected with an antigen-containing solution. The footpad on the left hind foot of each of the thirty mice in each phase, which was used as a control, was injected with about the same volume of a control solution, such as a sterile saline diluent, as the volume of antigen-containing solution that was injected into right hind footpad.

After a sufficient amount of time (e.g., about twenty-four hours) for the secondary immune response components of the immune system of each mouse to respond, each mouse was again anesthetized and the distances across right and left hind footpads were again measured. A significant amount of swelling, determined by an increase in the distance across a right hind footpad of a mouse from the initial measurement to the second measurement, is indicative of the occurrence of a delayed-type hypersensitivity reaction in that footpad.

The results of the mouse foot pad assays, and some accompanying analysis, are set forth in EXAMPLES 2 through 5 and 7:

Example 2

In the first phase of the study, the footpads on the right hind feet of the six mice of the negative control, or first group, exhibited, on average, about 6.35 micrometers more swelling about twenty-four hours after they were injected with the antigen solution than the swelling measured in the footpads of the left hind feet of these mice, which were merely inoculated with sterile saline.

The results for the negative control group during the second phase of the study are set forth in the following table:

TABLE 2

| Mouse | Foot (left/right) | Foot Pad (untreated) (micrometers) | Foot Pad (final) (micrometers) | Foot Pad (difference) (micrometers) |
|---|---|---|---|---|
| 1 | Left (control) | 1930.40 | 1955.80 | 25.40 |
|   | Right (test) | 1905.00 | 1930.40 | 25.40 |
| 2 | Left (control) | 1981.20 | 2006.60 | 25.40 |
|   | Right (test) | 2006.60 | 2057.40 | 50.80 |
| 3 | Left (control) | 2057.40 | 2057.40 | 0.00 |
|   | Right (test) | 2032.00 | 2057.40 | 25.40 |
| 4 | Left (control) | 2006.60 | 2032.00 | 25.40 |
|   | Right (test) | 2032.00 | 2057.40 | 25.40 |
| 5 | Left (control) | 1955.80 | 2006.60 | 50.80 |
|   | Right (test) | 1930.40 | 1955.80 | 25.40 |
| 6 | Left (control) | 1905.00 | 1930.40 | 25.40 |
|   | Right (test) | 1876.60 | 1955.80 | 76.20 |

Similar to the results from the first phase, the footpads of the right hind feet of the mice of the negative control group exhibited, on average, only 12.70 micrometers more swelling about twenty-four hours after antigen injection than the footpads of the left hind feet of the same mice exhibited twenty-four hours after sterile saline injection. As twenty-four hours is not a sufficient period of time for a mouse to mount a primary (i.e., antibody-mediated) immune response to the antigen, these insignificant differences in swelling show that the mice did not exhibit a significant secondary immune response to the antigen.

Example 3

In the first phase of the study, about twenty-four hours after they were injected with the antigen solution, the footpads on the right hind feet of the six mice of the second group of mice (which mice had previously been inoculated with a solution including 16% solids (w/v) colostrum at pH=4.0) swelled, on average, by 50.80 micrometers more than the swelling that was measured in the footpads of the left hind feet of these mice. These results indicate that there was a greater secondary, or delayed-type hypersensitivity, immune response in the footpads into which antigen was injected than in the footpads into which no antigen was injected, which were likely swollen merely because they were pierced by a needle.

In the second phase of the study, similar results were obtained, as set forth in the following table:

TABLE 3

| Mouse | Foot (left/right) | Foot Pad (untreated) (micrometers) | Foot Pad (final) (micrometers) | Foot Pad (difference) (micrometers) |
|---|---|---|---|---|
| 1 | Left (control) | 1955.80 | 2006.60 | 50.80 |
|   | Right (test) | 1981.20 | 2057.40 | 76.20 |
| 2 | Left (control) | 1930.40 | 2006.60 | 76.20 |
|   | Right (test) | 1955.80 | 2108.20 | 152.40 |
| 3 | Left (control) | 1955.80 | 2006.60 | 50.80 |
|   | Right (test) | 1981.20 | 2082.80 | 101.60 |
| 4 | Left (control) | 2032.00 | 2057.40 | 25.40 |
|   | Right (test) | 2057.40 | 2108.20 | 50.80 |
| 5 | Left (control) | 1930.40 | 2006.60 | 76.20 |
|   | Right (test) | 1955.80 | 2032.00 | 76.20 |
| 6 | Left (control) | 2057.40 | 2108.20 | 50.80 |
|   | Right (test) | 2032.00 | 2159.00 | 127.00 |

More specifically, the footpads of the right hind feet of the six mice of the second group swelled so that they measured, on average, 42.33 micrometers more than the swelling that was measured in the footpads of the left hind feet of these mice before and after inoculation of their foot pads with the antigen solution. The similar results between the first and second phases of the study indicate that, once a liquid solution that includes transfer factor has been heat sterilized, there is little or no change in the activity of the transfer factor after prolonged storage of the solution.

Example 4

The results for the third group of mice (which mice had previously been inoculated with a solution including 16% solids (w/v) colostrum at normal pH) were similar to the results for the second group in the first and second phases of the study.

In the first phase of the study, about twenty-four hours after the footpad injections, the antigen solution-inoculated footpads on the right hind feet of the six mice of the third group of mice swelled, on average, by 35.98 micrometers more than the swelling that was measured in the sterile saline-inoculated footpads of the left hind feet of these mice. These results indicate that there was a greater secondary, or delayed-type hypersensitivity, immune response in the footpads into which antigen was injected than in the footpads into which no antigen was injected, which were likely swollen merely because they were pierced by a needle.

In the second phase of the study, similar results were obtained, as set forth in the following table:

TABLE 4

| Mouse | Foot (left/right) | Foot Pad (untreated) (micrometers) | Foot Pad (final) (micrometers) | Foot Pad (difference) (micrometers) |
|---|---|---|---|---|
| 1 | Left (control) | 2006.60 | 2032.00 | 25.40 |
|   | Right (test) | 2032.00 | 2082.80 | 50.80 |
| 2 | Left (control) | 2057.40 | 2057.40 | 0.00 |
|   | Right (test) | 2006.60 | 2108.20 | 101.60 |

TABLE 4-continued

| Mouse | Foot (left/right) | Foot Pad (untreated) (micrometers) | Foot Pad (final) (micrometers) | Foot Pad (difference) (micrometers) |
|---|---|---|---|---|
| 3 | Left (control) | 1981.20 | 2006.60 | 25.40 |
|   | Right (test) | 2057.40 | 2082.80 | 25.40 |
| 4 | Left (control) | 2006.60 | 2057.40 | 50.80 |
|   | Right (test) | 2032.00 | 2082.80 | 50.80 |
| 5 | Left (control) | 2057.40 | 2082.80 | 25.40 |
|   | Right (test) | 2082.80 | 2159.00 | 76.20 |
| 6 | Left (control) | 2082.80 | 2108.20 | 25.40 |
|   | Right (test) | 2108.20 | 2159.00 | 50.80 |

These results show that the footpads of the right hind feet of the six mice of the third group swelled so that they measured, on average, 33.87 micrometers more than the swelling that was measured in the footpads of the left hind feet of these mice before and after inoculation of the foot pads with the antigen solution. The similar results between the first and second phases of the study indicate that, following prolonged storage, there was little or no change in the activity of the transfer factor in a heat-sterilized solution.

Example 5

These results were confirmed by the results that were obtained from the fourth group of mice. In particular, during the first phase of the study, the footpads of the right hind feet of mice in the fourth group (which included mice that had been inoculated with a diluted liquid colostrum fraction that was not heat sterilized) exhibited, on average, about 35.98 micrometers more swelling than the foot pads of left hind feet of these mice about twenty-four hours after these footpads had been inoculated with antigen solution and sterile saline, respectively.

Similar results were obtained during the second phase of the study, in which the average difference was 42.33 micrometers, as evidenced by the following data:

TABLE 5

| Mouse | Foot (left/right) | Foot Pad (untreated) (micrometers) | Foot Pad (final) (micrometers) | Foot Pad (difference) (micrometers) |
|---|---|---|---|---|
| 1 | Left (control) | 1955.80 | 2032.00 | 76.20 |
|   | Right (test) | 1981.20 | 2082.80 | 101.60 |
| 2 | Left (control) | 2006.60 | 2057.40 | 50.80 |
|   | Right (test) | 2032.00 | 2108.20 | 76.20 |
| 3 | Left (control) | 1955.80 | 2006.60 | 50.80 |
|   | Right (test) | 1930.40 | 2057.40 | 127.00 |
| 4 | Left (control) | 1955.80 | 2082.80 | 127.00 |
|   | Right (test) | 1905.00 | 2032.00 | 127.00 |
| 5 | Left (control) | 2032.00 | 2082.80 | 50.80 |
|   | Right (test) | 2057.40 | 2184.40 | 127.00 |
| 6 | Left (control) | 1955.80 | 1955.80 | 0.00 |
|   | Right (test) | 2006.60 | 2057.40 | 50.80 |

As these results are comparable to (i.e., not significantly greater than) those obtained with heat-sterilized solutions (see the results from EXAMPLES 3 and 4), it is apparent that heat sterilization of a solution that includes transfer factor does not significantly diminish or reduce the activity of the transfer factor.

Example 6

This conclusion was verified by data from another mouse footpad assay, in which six BALB/c mice were inoculated, behind the neck, with 0.5 ml of a solution including 16% solids (w/v) of a spray-dried colostrum fraction that had been reconstituted in distilled, deionized water. About twenty-four hours later, the mice were anesthetized with isoflurane, then footpads on their hind feet measured and inoculated in the manner described above (i.e., left footpad with sterile saline, right footpad with the antigen solution). After about another twenty-four hours, the footpads were again measured. The right footpads of these mice swelled, on average, about 42.33 micrometers more than the footpads on the left hind feet of these mice. This value is comparable to (i.e., not significantly different from) the differences noted above with respect to the second, third, and fourth groups of mice in both the first and second phases of the study detailed in EXAMPLES 2 through 5 and 7, further supporting the conclusion that heat sterilization of a solution that includes transfer factor, such as the solutions that were tested on the second and third groups of mice (EXAMPLES 3 and 4) does not have a significant adverse effect on the activity of the transfer factor.

Example 7

The fact that the transfer factor with which the mice were inoculated was responsible for the increased secondary immune response is supported by the results from the fifth group, or positive control group, of mice during the second phase of the study, as set forth in the following table:

TABLE 6

| Mouse | Foot (left/right) | Foot Pad (untreated) (micrometers) | Foot Pad (final) (micrometers) | Foot Pad (difference) (micrometers) |
|---|---|---|---|---|
| 1 | Left (control) | 1981.20 | 2006.60 | 25.40 |
|   | Right (test) | 2006.60 | 2082.80 | 76.20 |
| 2 | Left (control) | 1828.80 | 1854.20 | 25.40 |
|   | Right (test) | 1879.60 | 2082.80 | 203.20 |
| 3 | Left (control) | 1905.00 | 1930.40 | 25.40 |
|   | Right (test) | 1981.20 | 2082.80 | 101.60 |
| 4 | Left (control) | 2006.60 | 2057.40 | 50.80 |
|   | Right (test) | 2032.00 | 2184.40 | 152.40 |
| 5 | Left (control) | 2032.00 | 2057.40 | 25.40 |
|   | Right (test) | 2057.40 | 2184.40 | 127.00 |
| 6 | Left (control) | 2108.20 | 2108.20 | 0.00 |
|   | Right (test) | 2082.80 | 2184.40 | 101.60 |

These results, which show on average, 101.60 micrometers more swelling in the footpads that were inoculated with antigen solution over those that were inoculated with sterile saline, are similar to the 124.88 micrometer difference seen in the mice of the positive control group during the first phase of the mouse footpad study. The greater swelling in the antigen solution-inoculated footpads of the mice of the positive control group is indicative of a greater secondary immune response than that induced artificially by administration of transfer factor, as the mice of the positive control group had a sufficient period of time (i.e., two weeks) to generate their own transfer factor and, thus, to mount their own secondary immune response to the antigen.

Once an edible preparation of the present invention has been manufactured, it may be introduced into a clean or sterile container for subsequent transport and storage.

Example 8

In another study, mouse footpad assays were conducted to determine the effectiveness of transfer factor in heat-treated samples of a liquid solution that included transfer factor that had been stored for one year. In total, four samples were prepared, two each having a pH of about 4 and two each having a pH of about 7. All of the samples had been flash sterilized at a temperature of about 250° F. for about two seconds to about four seconds. The samples were subsequently stored for one year, with one each of the pH=4 and pH=7 samples having been stored at room temperature (which varied from about 65° F. to about 74° F.) and one each of the pH=4 and pH=7 samples having been refrigerated (at temperatures of about 40° F.). After one year, the samples were lyophilized. Prior to testing, the lyophilized samples were reconstituted to desired concentrations, then administered in the manner described above.

In a first sample, which included liquid having a pH of about 4 that was stored at room temperature, footpad swelling was, on average, 50.80 micrometers greater in footpads that had been injected with antigen versus footpads that had merely been injected with saline. These results were repeated in second (liquid of a pH of about 7 that was stored at room temperature), third (liquid of a pH of about 4 that was refrigerated), and fourth (liquid of a pH of about 7 that was refrigerated) samples, in which hind footpads that had been injected with antigen were, on average, respectively swollen 59.27, 67.73, and 63.50 micrometers more than hind footpads that were merely injected with saline.

Additionally, positive and negative controls were prepared as discussed above. In the positive control, the average difference in swelling between antigen-injected footpads and saline-injected footpads was 114.30 micrometers. In the negative control, the average difference in swelling between antigen-injected footpads and saline-injected footpads was only 38.10 micrometers.

Taken together, these data indicate that the increased swelling was due to the presence of transfer factor in the mice in the areas (hind footpads) into which antigen was introduced. Additionally, these data indicate that the transfer factor lost little or none of its effectiveness after heat-treatment and prolonged storage. The activity of transfer factor in refrigerated samples appears to have been slightly higher than the activity of transfer factor in the room temperature samples.

Further, it appears from the foregoing that the pH at which the transfer factor is maintained (about 4 or about 7) has little or no effect on its long term viability.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions, and modifications to the invention as disclosed herein which fall within the meaning and scope of the claims are to be embraced thereby.

What is claimed:

1. A nutritional supplement, comprising:
   a liquid fruit component of at least one oligoproanthocyanidin-containing fruit, the liquid fruit component comprising an oligoproanthocyanidin; and
   transfer factor dissolved in the liquid fruit component and capable of eliciting an immune response in the presence of the oligoproanthocyanidin.

2. The nutritional supplement of claim 1, wherein the liquid fruit component comprises fruit juice.

3. The nutritional supplement of claim 1, wherein the at least one oligoproanthocyanidin-containing fruit comprises açai.

4. The nutritional supplement of claim 3, wherein the liquid fruit component further comprises at least an extract of one or more of elderberry, grape, and pomegranate.

5. The nutritional supplement of claim 1, wherein the at least one oligoproanthocyanidin-containing fruit comprises at least one of açai, elderberry, grape, and pomegranate.

6. The nutritional supplement of claim 1, wherein the transfer factor comprises at least one of avian transfer factor and bovine transfer factor.

7. The nutritional supplement of claim 1, further comprising:
   at least one preservative.

8. The nutritional supplement of claim 7, wherein the at least one preservative comprises at least one of lactoferrin, lysozyme, and lactoperoxidase.

9. The nutritional supplement of claim 7, wherein the liquid fruit component and the transfer factor component are pasteurized.

10. A nutritional supplement, comprising:
    a fruit component including at least a portion of at least one oligoproanthocyanidin-containing fruit, the fruit component including an oligoproanthocyanidin;
    transfer factor capable of eliciting an immune response in the presence of the oligoproanthocyanidin; and
    a preservative.

11. The nutritional supplement of claim 10, in a liquid form.

12. The nutritional supplement of claim 11, wherein the fruit component comprises fruit juice.

13. The nutritional supplement of claim 10, in a solid form.

14. The nutritional supplement of claim 13, further comprising:
    a chewable base.

15. The nutritional supplement of claim 10, wherein the at least one oligoproanthocyanidin-containing fruit comprises açai.

16. The nutritional supplement of claim 15, wherein the fruit component further comprises at least a portion of one or more of elderberry, grape, and pomegranate.

17. The nutritional supplement of claim 10, wherein the at least one oligoproanthocyanidin-containing fruit comprises at least one of açai, elderberry, grape, and pomegranate.

18. The nutritional supplement of claim 10, wherein the transfer factor comprises at least one of avian transfer factor and bovine transfer factor.

19. The nutritional supplement of claim 10, wherein the fruit component and the transfer factor component are pasteurized.

20. The nutritional supplement of claim 10, wherein the at least one preservative component comprises at least one of lactoferrin, lysozyme, and lactoperoxidase.

* * * * *